United States Patent [19]
Spurr

[11] 3,933,718
[45] Jan. 20, 1976

[54] LOW VISCOSITY EMBEDDING MEDIUM

[75] Inventor: Arthur R. Spurr, Davis, Calif.

[73] Assignee: The Regents of the University of California, Berkeley, Calif.

[22] Filed: Apr. 23, 1974

[21] Appl. No.: 463,318

Related U.S. Application Data

[63] Continuation of Ser. No. 208,926, Dec. 16, 1971, abandoned, which is a continuation of Ser. No. 2,386, Jan. 12, 1970, abandoned.

[52] U.S. Cl. .... 260/30.4 EP; 260/830 TW; 260/831
[51] Int. Cl.² ......................................... C08K 5/15
[58] Field of Search....... 260/30.4 EP, 831, 830 TW

[56] References Cited
OTHER PUBLICATIONS

Harper, Electronic Packaging with Resins, 1961, pp. 58 & 59.

Helmreich et al., "Two Flexible Epoxy Resins," SPE Journal, Vol. 17, No. 6, pp. 583–586 (1961).
Potter, Epoxide Resins, 1970, pp. 126 & 127.

*Primary Examiner*—Donald E. Czaja
*Assistant Examiner*—S. M. Person
*Attorney, Agent, or Firm*—Phillips, Moore, Weissenberger Lempio & Strabala

[57] ABSTRACT

Microscopy specimens are infused with and embedded in a low viscosity medium whose composition comprises: a low viscosity epoxy resin, a moderately low viscosity epoxy flexibilizer, an anhydride hardener, and an accelerator. The composition's viscosity is low enough to permit thorough infusion into a wide range of specimens, including endosperms with a high lipid content, tissues with hard, lignified cell walls, and highly vacuolated parenchymatous tissues of ripe fruits.

6 Claims, No Drawings

LOW VISCOSITY EMBEDDING MEDIUM

This application is a continuation of application Ser. No. 208,926, filed Dec. 16, 1971, and now abandoned, which was a continuation of application Ser. No. 2,386, filed Jan. 12, 1970, also now abandoned.

BACKGROUND AND SUMMARY OF THE INVENTION

The present invention relates to embedding media for microscopy specimens and more particularly to a low viscosity embedding medium for numerous types of electron microscopy specimens.

In sectioning specimens for subsequent microscopic examination it is desirable to secure sections with the least amount of distortion or disruption of cell or tissue structures as they existed in the viable or original state. In order to preserve such structures it is the general practice to infuse the specimen before sectioning with a medium designed to firm up or reinforce such microstructures so that they will remain intact during the sectioning process and during subsequent handling while under examination.

Such embedding media range from the old paraffinic materials to more recently devised organic polymeric materials such as acrylics and epoxy compositions. Despite the improvement in composition of embedding media a continuing problem remains, i.e., complete infusion of the microstructures. For unless the embedding medium thoroughly penetrates into the minutest structure, distortion or disruption thereof will take place upon sectioning and subsequent handling.

Thorough infusion of the specimens is also complicated by the fact that while the medium must completely penetrate the specimen microstructures, it must also be resistant to fracturing upon sectioning, it must remain transparent to light or the electron beam, it must show no microstructure itself at the microscopy magnifications to be utilized, it must solidify or polymerize at temperatures low enough to prevent damage to the specimen structure or tissues, it must not damage the specimen microstructures upon polymerization, but it must solidify or polymerize to sufficient hardness to rigidly hold the specimen microstructures in position during sectioning and subsequent handling, and finally it must possess a reasonable "pot" life to permit infusion of a reasonable number of specimens or large specimen samples before solidification or polymerization takes place.

A new embedding medium has now been devised which fulfills all of the aforestated requirements as well as being of sufficiently low viscosity to thoroughly penetrate and infuse the minutest structures of a wide range of specimen tissues including problem materials such as the lipid storage endosperm of castor bean seeds and tomatoes, hard, lignified elements in vascular bundles of tomato leaves, as well as the soft, highly vacuolated, parenchymatous tissues of ripe tomato fruits.

Briefly the medium of the invention comprises low viscosity components comprising the following: a cycloaliphatic diepoxide, preferably vinyl cyclohexene dioxide; an epoxy resin flexibilizer, preferably diglycidyl ether of polypropylene glycol; an anhydride hardener, preferably nonenyl succinic anhydride; and an accelerator, preferably an alkyl alkanol amine such as dimethylamino-ethanol.

DETAILED DESCRIPTION OF THE INVENTION

The embedding medium of the invention comprises a low viscosity epoxy resin composition including an epoxy resin selected from the cycloaliphatic diepoxides, more specifically vinyl cyclohexene dioxide. This cycloaliphatic diepoxide is a clear liquid with a molecular weight of 140.18, an epoxide equivalent of 74–78 (grams of resin containing one gram equivalent of epoxide), and a specific gravity of 1.10 at 20°C. It has a viscosity that is quite low for epoxy resins, that is 7.8 centipoises at 25°C.

The vinyl cyclohexene dioxide has the following chemical structure:

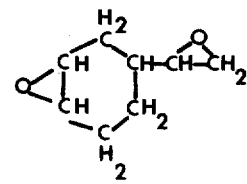

A flexibilizer is added to the embedding medium composition in order to prevent undue hardness and brittleness of the specimen castings. The diglycidyl ether of polypropylene glycol epoxy resin is quite suitable as the flexibilizer. This resin has a molecular weight of about 380, a specific gravity of 1.14 at 25° C. and has a moderately low viscosity of 30–60 centipoises at 25° C.

It is considered as a flexible epoxy resin by virtue of its long aliphatic structure derived from the condensation of polypropylene glycol and epichlorohydrin. Its theoretical structure is:

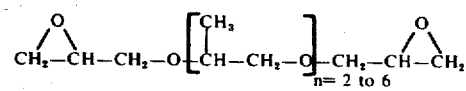

From the above formula it should be noted that the number of propylene glycol units per molecule of the diglycidyl ether may vary from as little as 2 to as high as 6. Such numbers are however understood to be the average of propylene glycol units since the flexibilizer normally contains a mixture of sUch noted molecules. Generally, however, n averages 4. But any such diglycidyl ether of polypropylene glycol having an average of propylene glycol units in the range of from 2 to 6 is satisfactory for use in the invention composition.

A hardener has been found necessary in the embedding composition. The branched alkenyl succinic anhydrides based on tripropylene are preferred. More specifically nonenyl succinic anhydride is particularly preferred since it is essentially water-white in color and the resultant castings are lower in color than those made with hardeners of other types.

Nonenyl succinic anhydride has a molecular weight of 224, a specific gravity of 1.01 and has a structural formula:

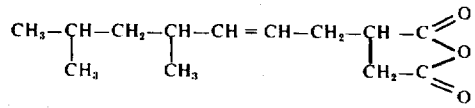

The final component of the embedding medium is an accelerator. The alkyl alkanol amines are suitable for this purpose, with dimethylaminoethanol being preferred. Dimethylaminoethanol is a clear liquid with a viscosity of 3.32 centipoises at 25°C. and a specific gravity of 0.89 at 20°C. It has the structure:

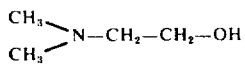

and is quite effective in inducing a rapid cure of the embedding composition at temperatures of 70°C. and above, even when used in low concentrations of about 1.0 percent by weight of the total resin components.

For general infusion and embedding use, a composition of the above components has been found most useful:

|  | parts by weight |
|---|---|
| Vinyl cyclohexene dioxide | 10 |
| Diglycidyl ether of poly-propylene glycol | 6 |
| Nonenyl succinic anhydride | 26 |
| Dimethylamino ethanol | 0.4 |

The above composition has a "pot" life of three to four days and has a viscosity of about 60 centipoises at 25°C. immediately after mixing and a viscosity of 140 centipoises at 25°C. 24 hours later.

The medium is simply prepared by weighing out suitable amounts of each of the components and then adding each of them in turn to a suitable container. The two epoxy components and the anhydride hardener are gently agitated upon addition. The mixture is further shaken briefly after addition of the alkyl alkanol amine accelerator, but this should be done so as to minimize the entrainment of air. A light vacuum may be applied to the composition to facilitate removal of any entrained air.

The completed composition may then be used immediately for infusing specimens. However the composition will remain fluid for several days if held at ambient room temperatures. Alternatively, the composition may be frozen solid in a deep freezer for an extended period of time. Upon thawing the composition can be used to infuse and embed specimens in the normal manner.

The composition of the invention may be modified to a considerable extent if it is desired to obtain harder or softer castings, effect a more rapid cure or polymerization, maintain a longer "pot" life, or infuse with a composition of lower viscosity than the composition set forth above. Thus reducing the diglycidyl ether of polypropylene glycol resin to but 4 parts by weight in the composition will yield a composition much harder when polymerized. If the same resin is increased to 8 parts by weight, a soft curing medium will result. The cure rate and "pot" life of the composition may also be modified by altering the relative amount of accelerator in the composition. Thus if the dimethylaminoethanol is increased to about 1.0 part by weight in the standard composition as set forth above, the infused specimen will cure in approximately 3 hours at 70°C. as opposed to a cure of approximately 8 hours at 70°C for the standard composition. The "rapid" cure composition has a "pot" life of approximately 2 days as opposed to a 3–4 day "pot" life for the standard composition. Conversely, if the dimethylaminoethanol accelerator is reduced to about 0.2 parts by weight in the composition, the cure time rises to approximately 16 hours at 70°C. while the "pot" life is extended to about 7 days.

Of course, it is apparent that variations in the composition of the embedding medium may be made from those specifically set forth above with a corresponding change in resultant hardness, cure time or "pot" life.

SPECIMEN PREPARATION

A specimen to be infused with and embedded in the composition of the invention is initially dehydrated with any of the commonly utilized dehydrating fluids such as acetone, dioxan, ethanol, hexylene glycol, isopropyl alcohol, propylene oxide or tertiary butyl alcohol. All of the above noted dehydrating fluids are completely miscible with the embedding medium.

In any event, the specimen is thoroughly dehydrated in the selected fluid by immersion therein for a length of time sufficient to insure thorough infusion and dehydration of the tissues. It is often advantageous to carry out several immersions in increasingly stronger concentrations of the dehydrating fluid. The final dehydration is carried out in a small amount of excess fluid.

Embedding medium is then added to the specimen in the dehydrating fluid in an amount about equal to the remaining dehydrating fluid. The fluid and medium with the specimen therein are swirled together thoroughly so as to thoroughly mix the liquid components and the entire mixture is permitted to stand for about ½ hour. Another equal quantity of embedding medium is then added to the previous mixture, is mixed, and then permitted to stand for an additional ½ hour.

The mixture of dehydrating fluid and embedding medium is then decanted from the specimen and a third amount of embedding medium is then added whereby the specimen is now in 100 percent embedding medium.

The specimen is permitted to stand in the embedding medium for a period of time regarded as sufficient to permit thorough infusion, at least for several hours or so. A second change of embedding fluid is made and further infusion is permitted to take place.

After thorough infusion is considered to have taken place the specimen in an excess amount of medium is polymerized at about 70°C. for 8 or more hours. Upon polymerization, the medium and embedded specimen cure to a solid which may subsequently be handled and sectioned in the conventional manner.

Variations in dehydration, infusion, and embedding of the specimens will be readily apparent to those skilled in the art.

What is claimed is:

1. In an embedding medium for infusing the cells of biological specimens, polymerizable to a hard, tough, transparent polymer without disruption of said cells, the improvement comprising employing in said medium about 10 parts by weight of a polymerizable cycloaliphatic diepoxide having a viscosity of less than about 8 centipoise at 25° C., about 4 to 8 parts by weight of an epoxy resin flexibilizer product, derived from the condensation of a polypropylene glycol having a degree of polymerization of from about 2 to 6 with epichlorohydrin, and having a viscosity of less than about 60 centipoises at 25° C., about 26 parts by weight of an anhydride hardener having a viscosity of less than about 120 centipoises at 25°C., and about 0.2 to 1.0 parts by weight of an alkyl alkanol amine accelerator having a viscosity of less than about 4 centipoises at 25° C.

2. The embedding medium of claim 1 wherein said diepoxide resin is vinyl cyclohexene dioxide.

3. The embedding medium of claim 1 wherein the epoxy resin flexibilizer is diglycidyl ether of polypropylene glycol.

4. The embedding medium of claim 1 wherein said anhydride hardener is an alkenyl succinic anhydride.

5. The embedding medium of claim 4 wherein the alkenyl succinic anhydride is nonenyl succinic anhydride.

6. The embedding medium of claim 1 wherein the alkyl alkanol amine accelerator is dimethylaminoethanol.

* * * * *